United States Patent [19]

Rudella

[11] Patent Number: 5,268,179
[45] Date of Patent: Dec. 7, 1993

[54] ULTRASONICALLY SEALED TRANSDERMAL DRUG DELIVERY SYSTEMS

[75] Inventor: Michael D. Rudella, Cedar Knolls, N.J.

[73] Assignee: Ciba-Geigy Corporation, Ardsley, N.Y.

[21] Appl. No.: 837,456

[22] Filed: Feb. 14, 1992

[51] Int. Cl.⁵ .............................................. A61F 13/00
[52] U.S. Cl. ................................ 424/449; 424/448; 156/73.1; 206/440
[58] Field of Search ............... 424/449, 448; 156/73.1, 156/73.2, 73.3; 206/440

[56] References Cited

U.S. PATENT DOCUMENTS

| | | | |
|---|---|---|---|
| 3,598,122 | 11/1970 | Zaffaroni | 128/268 |
| 3,598,123 | 8/1971 | Zaffaroni | 128/268 |
| 3,731,683 | 5/1973 | Zaffaroni | 128/268 |
| 3,734,097 | 5/1973 | Zaffaroni | 128/268 |
| 3,742,951 | 11/1973 | Zaffaroni | 128/268 |
| 3,797,494 | 3/1974 | Zaffaroni | 128/268 |
| 3,948,254 | 4/1976 | Zaffaroni | 128/127 |
| 3,996,934 | 12/1976 | Zaffaroni | 128/268 |
| 4,264,008 | 8/1981 | Kozlow | 206/441 |
| 4,284,444 | 8/1981 | Bernstein et al. | 156/60 |
| 4,304,333 | 12/1981 | Kozlow | 206/441 |
| 4,460,372 | 7/1984 | Compbell et al. | 604/897 |
| 4,588,580 | 5/1986 | Gale et al. | 424/21 |
| 4,597,961 | 7/1986 | Etscora | 424/28 |
| 4,666,441 | 5/1987 | Andriola | 604/897 |
| 4,667,665 | 5/1987 | Blanco | 128/156 |
| 4,686,136 | 8/1987 | Homonoff | 428/286 |
| 4,725,473 | 2/1988 | Van Gompel | 428/156 |
| 4,743,249 | 5/1988 | Loveland | 424/447 |
| 4,784,892 | 11/1988 | Storey | 428/172 |
| 4,823,783 | 4/1989 | Willhite | 128/156 |
| 4,911,707 | 3/1990 | Heiber et al. | 424/449 |
| 4,915,950 | 4/1990 | Miranda et al. | 424/448 |
| 4,917,676 | 4/1990 | Heiber et al. | 424/449 |
| 5,016,652 | 5/1991 | Rose et al. | 131/270 |
| 5,077,104 | 12/1991 | Hunt | 428/34.3 |

Primary Examiner—Thurman K. Page
Assistant Examiner—D. Gabrielle Phelan
Attorney, Agent, or Firm—Irving M. Fishman; Karen G. Kaiser

[57] ABSTRACT

A method of sealing transdermal drug delivery system components together which comprises contacting the surfaces of the components to be sealed together with each other and exposing the contacted surfaces to ultrasonic forces while said surfaces are still in contact to produce a seal of said surfaces in a predetermined manner.

11 Claims, 5 Drawing Sheets

ULTRASONICALLY SEALED TRANSDERMAL DRUG DELIVERY SYSTEMS

FIELD OF THE INVENTION

The present invention relates to the field of transdermal drug delivery device manufacture and construction. More particularly, it relates to the area of sealing various components of transdermal drug delivery devices to each other. The invention also relates to the area of ultrasonic welding and the range of technologies to which such welding can be adapted.

BACKGROUND OF THE INVENTION

Transdermal drug delivery devices have been in the literature for some time now and are seen to be of a number of different basic constructions. In their simplest forms there are the strict matrix monolith type devices and the membrane "sack" type devices. The simple strict monolith type has an active agent which is contained within a solid or semi-solid (capable of retaining its shape under light to moderately applied pressure) which is cast on or adhered to a backing layer impermeable to the passage of active agent. An adhesive may be only on or around the perimeter of or over the entire exposed surface (opposite that adjacent the backing layer) of the active agent containing layer. The simple "sack" type device has an active agent impermeable layer and a second layer (active agent permeable) affixed thereto such that the two layers define an active agent bulk reservoir for containing an active agent formulation. See especially U.S. Pat. Nos. 3,598,122; 3,598,123; 3,731,683; 3,734,097; 3,742,951; 3,797,494; 3,948,254; 3,996,934; 4,284,444; 4,597,961; 4,666,441; 4,911,77; 4,915,950; 4,917,676; 4,460,372; 4,588,580; 4,597,961; 4,743,249; and 5,016,652; all of which are incorporated herein by reference.

In most all cases of the "sack" type transdermal drug delivery devices there are at least two components which must be sealed together, usually with the active agent or active agent formulation in place during the sealing operation. In many instances, the strict monolith type of device, the monolithic material is not adhesive in its own right or its adhesive properties are insufficient for the needs of commercial products. In these cases, the active agent containing material must be affixed to the backing layer by some alternative means, such as sealing, or adhering it via an adhesive, or overlayering it with another layer which overlayer is affixed to the backing (creating a hybrid between the "sack" type and strick monolith type devices).

In general the above mentioned devices have used adhesives, heat sealing techniques, and pressure sealing techniques, either alone or in various combinations when sealing of components has been needed for transdermal drug delivery devices. While these techniques have indeed been found acceptable for obtaining product which will meet regulatory approval and quality assurance requirements, there are significant drawbacks involved that, if overcome, would make the manufacture of such devices cheaper, more efficient, and the devices themselves more reliable.

For example, the range of adhesives that will assure suitable integrity of seal areas and which will not affect active agent formulation components or their delivery from the reservoir (whether a "sack" type reservoir or monolithic one) are few indeed. Adhesives useful for seal purposes must be impermeable to active agent formulation so as to retain the active agent formulation within the device and not create a reservoir to which the active agent will preferentially migrate during storage. Such migration, should it occur, would result in the delivery characteristics differing from those for which the product was designed or introduce an additional possibility for batch-to-batch variation in results. Neither of these situations is desired even if the differences in results introduced fall within tolerance levels for meeting regulatory and quality assurance performance characteristics.

Active agent impermeable adhesives cannot be used for sealing purposes in all instances either. Again, there is the problem of chemical interaction with the active agent formulation itself, thereby limiting the number of adhesives to be employed. Secondly, if the adhesive inadvertently gets onto the portion through which the active agent is intended to diffuse, the delivery characteristics of the device will vary from the intended performance characteristics.

Pressure sealing eliminates the problems inherent in the chemical sealing, since there is no concern for chemical interaction between the sealing means and the active agent formulation and there is no concern for inappropriate migration of active agent into the sealing means. However, pressure seals have there own problems associated with them. Simply put, in the process of applying the pressure seal, the active agent formulation can easily be displaced and the materials being sealed can shear. Furthermore, in an effort to avoid inadvertent displacement of the active agent formulation, the seal might be placed at a slightly further point from the center, resulting in a space in which the active agent formulation might migrate within the reservoir area. This could result in differences in performance of the device depending upon orientation of the device during storage and use. Typical pressures used to generate such pressure seals are in the range of 500 lbs to 1200 lbs.

The third sealing technique, heat sealing, also overcomes the problems associated with adhesive sealing, but introduces other problem areas. Again, these problems set forth below, do not prohibit the ability to meet the regulatory and quality assurance requirements associated with commercial products, but they introduce potential variables which preferrentially should be eliminated or at least reduced to increase the efficiency of manufacture and reduce the number of reject units.

In the heat sealing operation (or thermal-die process) a steel sealing die of specified geometry is heated to a temperature range significantly greater than the melting point of the thermoplastic materials being sealed together. High die temperatures are necessary to insure heat penetration through the thermoplastic materials and induce melt at the seal area. The problems inherent in this process are that excessive heat causes the laminate materials to shrink and distort, machine speed and temperature of the die are proportionally related so that high die temperatures are needed for high speed operation, the laminate material with the lowest melting point may flow out of the seal area before the seal can be formed so that the thermal bond is weakened, and the melted thermoplastic material remains in a hydraulic state for a brief period after the hot die is retracted during which tension forces may cause the laminate material to separate thereby weakening the seal. Finally, heat seal systems are limited to those components (including active agent formulation) which can withstand the temperatures applied without appreciable degredation.

OBJECTS OF THE INVENTION

It is therefore an object of the invention to provide a means for sealing transdermal drug delivery systems which avoid the above problems of the existing sealing techniques.

It is another object of the invention to provide a transdermal drug delivery system sealing means which reduces the percentage of reject systems in commercial production over those prepared using the former techniques set out above.

It is yet another object of the invention to provide a transdermal drug delivery system which reduces energy input requirements over heat seal systems.

It is still another object of the invention to provide a transdermal drug delivery system sealing means which allow high machine speed sealing of such systems without excessive heating.

It is another object of the invention to provide for a sealing means for transdermal drug delivery systems which allow for use of a wider variety in materials suitable for use in the various components of the system while still being suited to high speed manufacture.

SUMMARY OF THE INVENTION

These and other objects are surprisingly achieved by a method of sealing components of a transdermal drug delivery system to one another utilizing ultrasonic welding.

DETAILED DESCRIPTION OF THE INVENTION AND DRAWINGS

Figure 1:
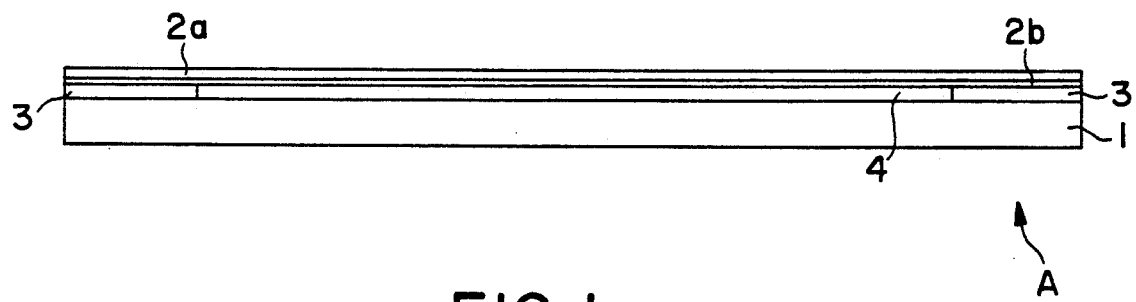
FIG. 1 is a typical "sack" type transdermal drug delivery device.

The invention is a method of making a transdermal drug delivery device (see for example FIG. 1) where the device (A) has a backing layer (1) and a second layer (2), said second layer contacting said backing layer and adhered thereto with a seal (3), said device further comprising an active agent located within said second layer or within a region defined by said backing layer and said second layer (i.e. a reservoir (4)), wherein said backing layer (1) is impermeable to said active agent and said second layer (2) is permeable to said active agent or an activated form of said active agent, said method comprising forming said seal ultrasonically. Each of layers (1) and (2) may be a single layer or a multilaminate. Frequently, layer (2) is a membrane (2b) and unless the second layer is already adhesive in nature, an adhesive (2a) is needed, either in a peripheral region or over a portion of surface of the second layer distal to the backing, or adhesive in both such areas. A release liner (not shown) covers the exposed portion of layer (2) until removed during the process of applying the transdermal device to a patient. In a simple statement, the invention is the fabrication of a transdermal drug delivery system which needs a seal by forming the seal ultrasonically.

Virtually any transdermal device that needs a seal between ultrasonically sealable components can be used in the invention. Such transdermal drug delivery systems and devices are shown using either chemical (adhesive), pressure, or heat sealing means in the aforementioned U.S. Patents, all of which are incorporated herein by reference.

Figure 6:
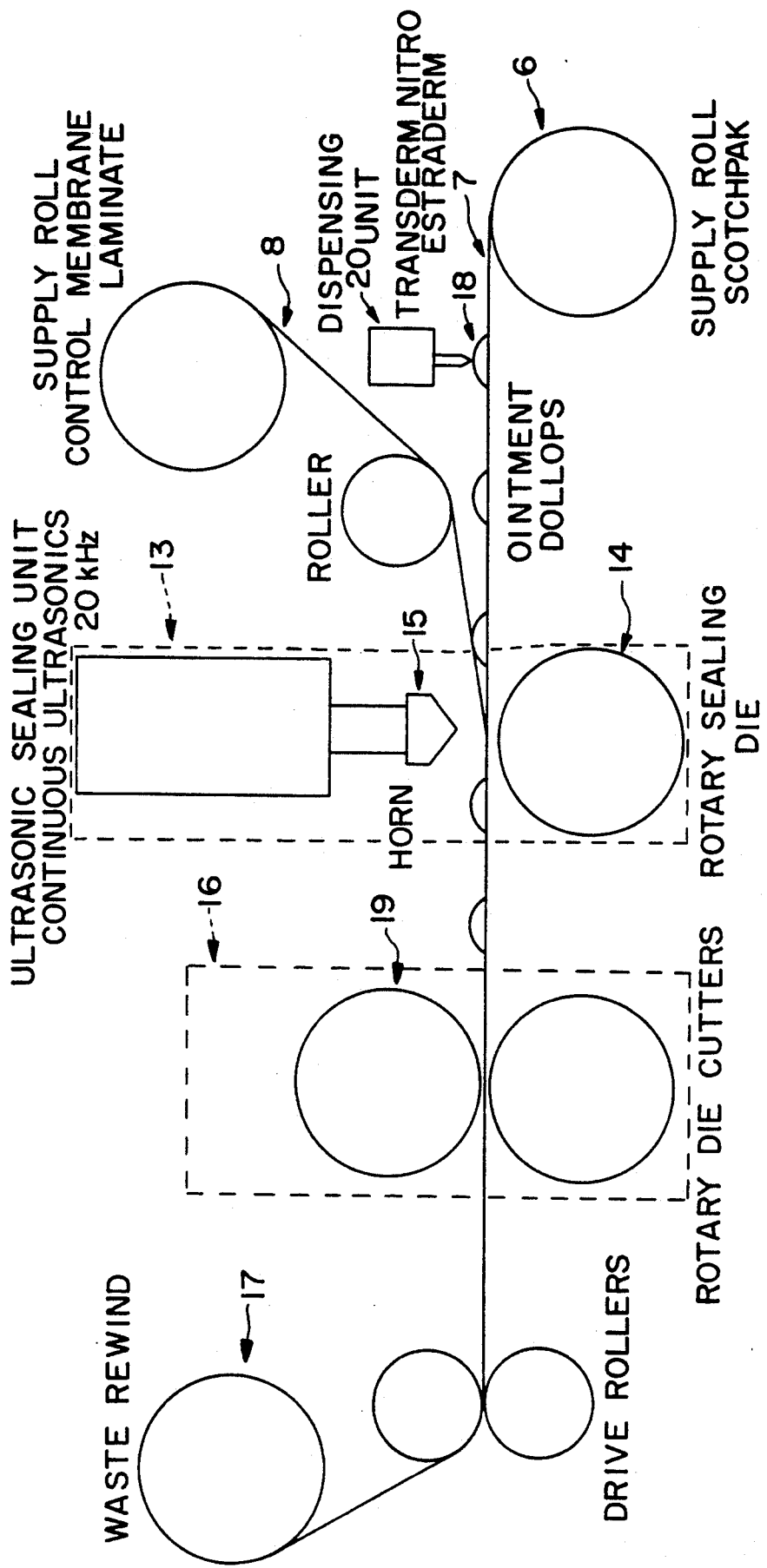
FIG. 6 illustrates a continuous application method of making transdermal devices according to the invention.
Figure 7:
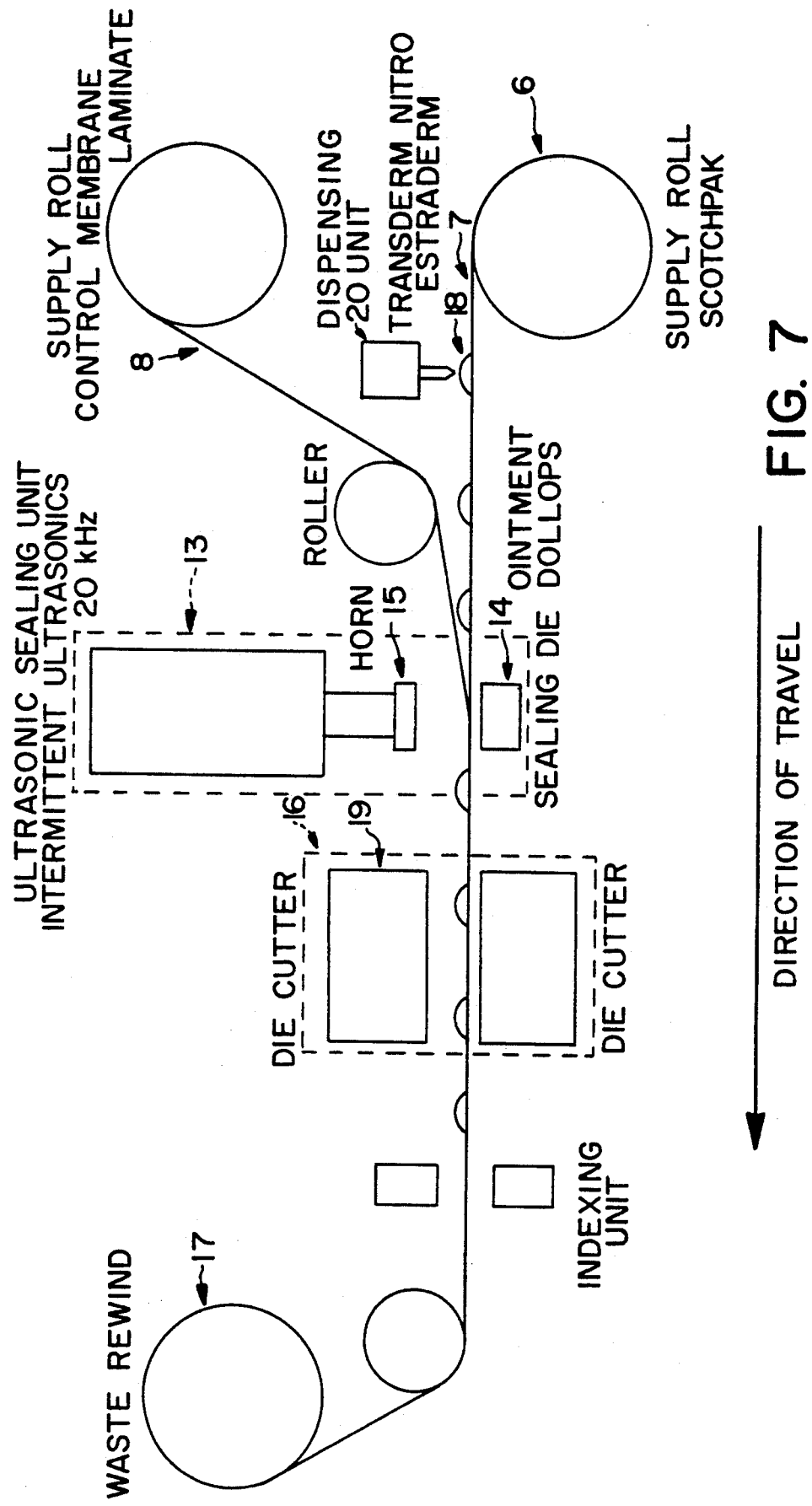
FIG. 7 illustrates an intermittant application method of making transdermal devices according to the present invention.

FIGS. 6 and 7 will be described here in greater detail with respect to the specific Examples. Ultrasonically sealable materials useful for the various components being sealed by the invention method include, without limitation, thermoplastic films. Preferably, these thermoplastics are either amorphous or crystalline in nature. Highly preferred crystalline films for use in the invention include, without limitation, ethylene-vinyl acetate, fluoropolymers, polyamides, polybutylene, polyester, polypropylene, polyethylene, poly(vinyl acetate) and copolymers of mixtures of the monomers therein. For the present purposes, copolymers include polymers having 2 or more different monomers selected from the monomers of the polymers in the previous sentence. Highly preferred amorphous materials include, without limitation, acrylic cellulose, polystyrene, poly(vinyl chloride), poly(vinyl dichloride), and copolymers containing at least two different monomers selected from the monomers of the forgoing amorphous polymers. Most highly preferred materials include, without limitation, ethylene-vinyl acetate, polyester, and polyethylene.

When either the backing layer or the second layer is itself a multilaminate, only the surfaces thereof which contact the other need be of the ultrasonically sealable material useful in the present invention. However, if desired, any of the other components of the multilaminates may be ultrasonically sealable.

Within each of these groups one of ordinary skill would known which are active agent or activated active agent permeable and which are active agent or activated active agent impermeable for a particular purpose. In the alternative, those of ordinary skill would readily be able to test the component materials to determine the permeability to a particular active agent, activated agent, and other active agent formulation components.

In the above description, any layer or material described generally may be a single material or a composite laminate wherein at least one component of the laminate is the material described above and is still in a position to accomplish the results intended. For example, wherever an ultrasonically sealable material is indicated, that material may be a single material or a laminate thereof with other materials provided the portion of such ultrasonically sealable material which is intended to be ultrasonically sealed is still available for such sealing. Where a laminate contains more than one ultrasonically sealable material therein, only one of such ultrasonically available materials need be available for forming the seal according to the invention.

Active agents and active agent precursors may be selected from any compound which is transdermally administrable and systemically active per se or metabolized in vivo to an active agent. The active agent and active agent precursors may also be selected from dermally active agents and their precursors. These materials are, without limitation, preferably selected from: antitubercular agents, such as isoniazid and rifampin; analgesics such as fentanyl and sufentanyl; muscle relaxants, such as baclofen; β-adrenergic receptor agonists and antiasthmatics, such as theophylline, formoterol, and terbutaline; steroids, such as estradiol, progesterone, methyltestosterone, and desoxycorticosterone; anticholinergics, such as scopolamine and methscopolamine; vasodilators, such as nitroglycerine; antihypertensives, such as metoprolol; antihistamines, such as tripolidine, tripelenamine, and diphenhydramine; cholinergic agents, such as arecoline; CNS stimulants, such as methylphenidate and nikethimide; angeotensin converting enzyme inhibitors such as benazepril, and benazeprilat; nicotine, physostigmine, and naloxone.

A preferred class of drugs for use in the systems prepared by the present invention method is fentanyl, sufentanyl, terbutaline, formoterol, theophylline, estradiol, progesterone, scopolamine, nitroglycerine, tripolidine, tripelenamine, diphenhydramine, arecoline, nicotine, benazepril, and benazeprilat. A still more preferred group includes: arecoline, nicotine, progesterone, triprolidine, diphenhydramine, formoterol, scopolamine, nitroglycerin, and estradiol. A most preferred group for use in the systems made by the present invention include: arecoline, nicotine, scopolamine, nitroglycerin and estradiol.

In the construction of the transdermal systems according to the present invention, the ultrasonically sealable components are brought in contact and an ultrasonic frequency is applied so as to cause sealing in the contact region. The frequency used is in the range of about 18 kHz to about 22 kHz, preferably about 19 kHz to about 21 kHz, more preferably about 20 kHz. The ultrasonic frequency can be applied for varying lengths of time, and, without limitation, is preferably applied for about 350 msec to about 950 msec, more preferably for about 450 msec to about 750 msec. In a highly preferred variation, a pressure is also applied in the seal area during a substantial portion of the time the ultrasonic frequency is applied. This force is, without limitation, preferably about 318 lb to about 566 lb, more preferably about 353 lb to about 495 lb, most preferably about 389 lb to 459 lb. Lesser pressures are also acceptable, if desired.

All other components of the transdermal systems of the invention may be chosen as appropriate from the transdermal patent literature cited above an incorporated herein by reference. Currently marketed transdermal administration devices which can be sealed with the present invention can be found in the 1991 Edition of the Physician's Desk reference.

Since the ultrasonic sealing technique is amenable to precise control, it is also suitable for forming preferentially burstable seals in transdermal devices according to U.S. Pat. Nos. 4,666,441, 4,917,676 and 4,911,707. Preferentially weaker seals (intended for bursting) can be made by separately controlling the ultrasonic forces applied to specific areas of the seal regions. Utilizing shorter ultrasonic frequency application times, and less intense pressures than for the non-burstable seals will result in preferentially burstable seals as desired. Where pressure is not used to seal the system, the ultrasonic sealing frequency application time should not be greater than 90% of the value used for the main seals, preferably not greater than 75%, and most preferably not greater than 60%, to create the burstable seals. Where pressure is simultaneously used with the ultrasonics to seal the main seals, the burstable seals can be created using pressures and ultrasonic sealing frequency application times, the product of which is not greater than 90%, preferably not greater than 75%, most preferably not greater than 60%, of the product of the pressure and ultrasonic frequency application time used for the main seals.

Figure 2:
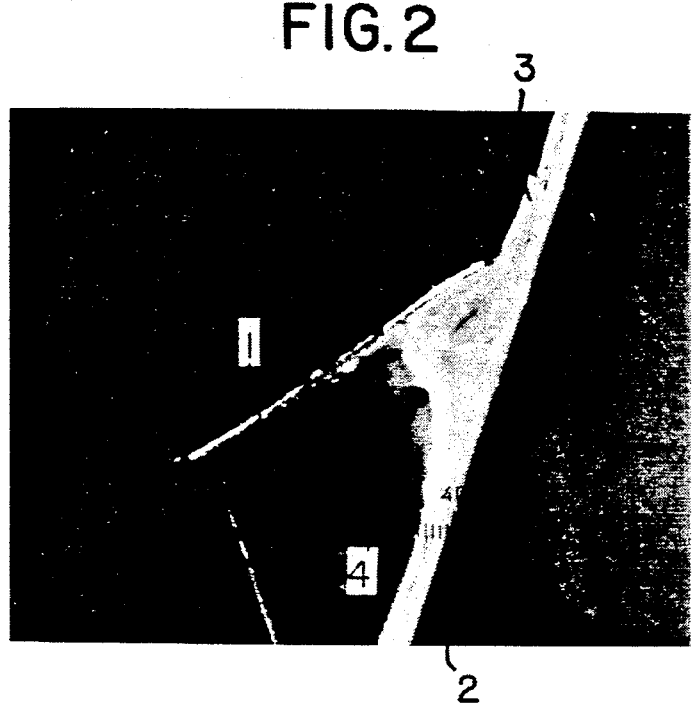
FIGS. 2-3 are photocopies of photographs of the seal portion of ultrasonically sealed transdermal drug delivery devices.
Figure 3:
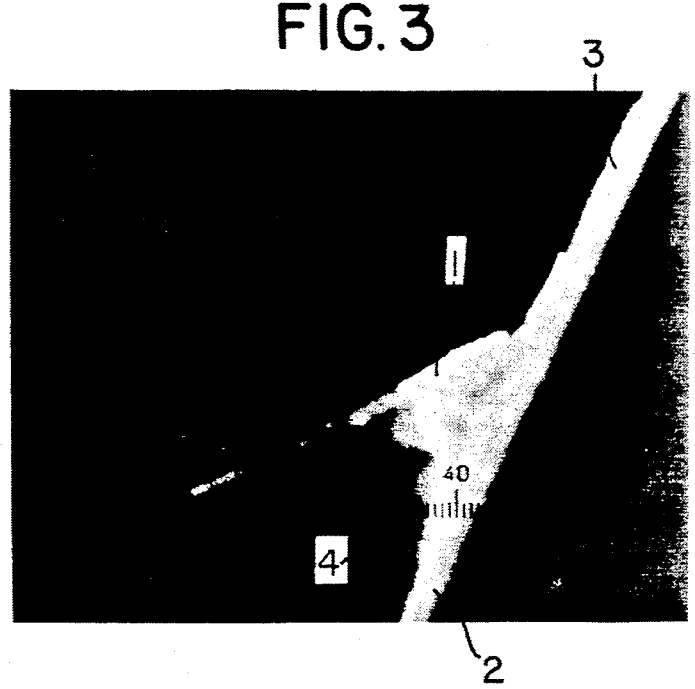
Figure 4:
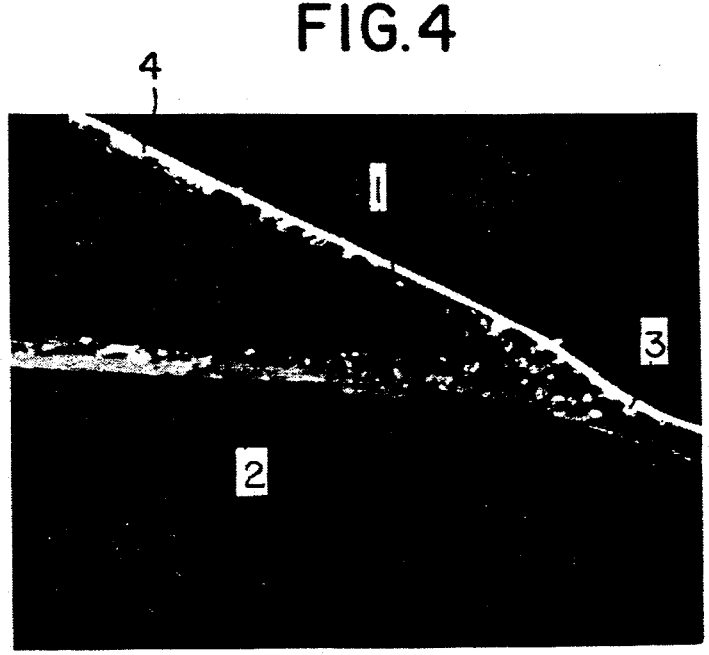
FIGS. 4-5 are photocopies of photographs of the seal portion of heat sealed transdermal drug delivery devices.
Figure 5:
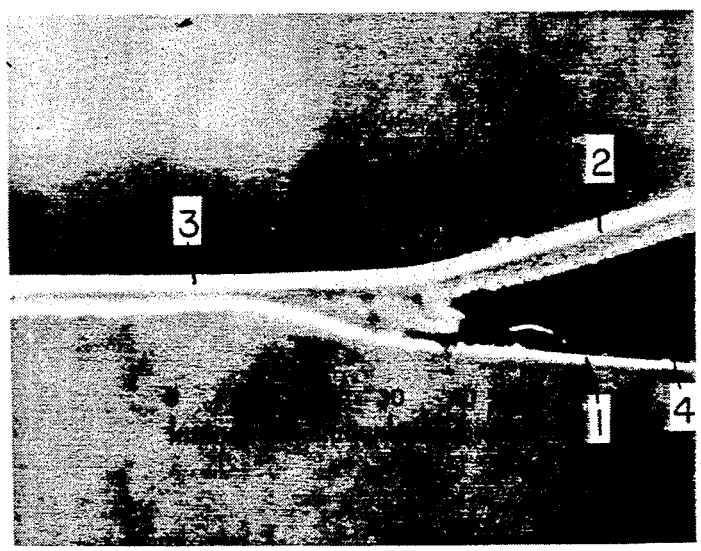

FIGS. 2-3 show seals of transdermal devices obtained using the present invention. FIGS. 4-5 show seals of corresponding transdermals sealed using heat sealing techniques. In each of FIGS. 2-5, the structures shown are backing layer (1), second layer (2), seal region (3), and reservoir (4).

FIGS. 6 and 7 are discussed in detail with respect to the following Examples.

EXAMPLES

The following Examples are for illustrative purposes only and do not limit the scope of the claimed invention.

Example 1

This Example is directed with especially to FIGS. 6 and 7. These Figures differ from each other in that FIG. 6 relates to a continuous motion fabrication machine and FIG. 7 relates to an intermittant motion machine. An ultrasonically sealable laminate 7 (impermeable to nitroglycerine), available under the tradename Scotchpack from 3M, corresponding to backing layer 1 (comprising a pigmented polyethylene, a polyester, vapor coated aluminum oxide, ethylene-vinyl acetate), is dispensed from lower mill roll unwinder 6 and introduced into a transdermal fabrication machine 12. An ultrasonically sealable laminate 8, (comprising an ethylene-vinyl acetate copylymer film, corresponding to second layer 2, a silicon adhesive 9, and a polyester release liner 10) is dispensed from upper mill roll unwinder 11 and introduced into the transdermal fabrication machine 12.

As laminates 7 and 8 are pulled through the transdermal fabrication machine 12, a nitroglycerine containing formulation 18 is dispensed by dispensing unit 20 onto the ultrasonically sealable surface of laminate 7. After deposition of the nitroglycerine formulation, the ultrasonically sealable surface of laminate 8 is brought in contact with the ultrasonically sealable surface of laminate 7 with the nitroglycerine formulation on a portion thereof. The loosely fitted system is then brought to ultrasonic sealing unit 13, where the nitroglycerine formulation deposition area is precisely alligned with predetermined seal patterns on male rotary sealing die 14, located below laminate 7. Horn 15, located above laminate 8 (and alligned with die 14) and die 14 approach each other so as to apply a force of about 400 lbs while horn 15 generates an ultrasonic force of about 20 kHz to effect sealing. After sealing, the sealed systems move to die cutting station 16 where the finished transdermal systems are cut from the films by rotary die cutters 19 and the waste is removed by take up roller 17.

Example 2

This Example is directed with especially to FIGS. 6 and 7. An ultrasonically sealable laminate 7 (impermeable to estradiol), corresponding to backing layer 1 (comprising a a polyester and ethylene-vinyl acetate), is dispensed from lower mill roll unwinder 6 and introduced into a transdermal fabrication machine 12. An ultrasonically sealable laminate 8, (comprising an ethylene-vinyl acetate copylymer film, corresponding to second layer 2, a silicon adhesive 9, and a polyester release liner 10) is dispensed from upper mill roll unwinder 11 and introduced into the transdermal fabrication machine 12.

As laminates 7 and 8 are pulled through the transdermal fabrication machine 12, an estradiol containing formulation 18 is dispensed by dispensing unit 20 onto the ultrasonically sealable surface of laminate 7. After deposition of the estradiol formulation, the ultrasonically sealable surface of laminate 8 is brought in contact with the ultrasonically sealable surface of laminate 7 with the estradiol formulation on a portion thereof. The loosely fitted system is then brought to ultrasonic sealing unit 13, where the estradiol formulation deposition area is precisely alligned with predetermined seal patterns on male rotary sealing die 14, located below laminate 7. Horn 15, located above laminate 8 (and alligned with die 14) and die 14 approach each other so as to apply a force of about 400 lbs while horn 15 generates an ultrasonic force of about 20 kHz for about 600 msec to effect sealing. After sealing, the sealed systems move to die cutting station 16 where the finished transdermal systems are cut from the films by rotary die cutters 19 and the waste is removed by take up roller 17.

I claim:

1. A method of making a transdermal drug delivery device said device comprising a backing layer and a second layer, said second layer contacting said backing layer and adhered thereto with a seal, said device further comprising an active agent located within said second layer or within a region defined by said backing layer and said second layer, wherein said backing layer is impermeable to said active agent and said second layer is permeable to said active agent or an activated form of said active agent, said method comprising forming said seal ultrasonically by applying an ultrasonic frequency of about 18 kHz to about 22 kHz in a desired sealing pattern for a period of about 250 msec to about 950 msec along with a substantially simultaneous pressure of about 318 lbs to about 566 lbs.

2. A transdermal drug delivery device produced by the method of claim 1.

3. The method of claim 1 wherein said transdermal drug delivery device backing layer is a first laminate of an active agent impermeable member and an ultrasonically sealable first member and wherein said second layer contacts said ultrasonically sealable first member of said first laminate.

4. The method of claim 1 wherein said second layer is a laminate of a non-ultrasonically sealable second member and an ultrasonically sealable third member, wherein said ultrasonically sealable third member of said second layer contacts said backing layer, and said ultrasonically sealable third member and said non-ultrasonically second member are permeable to said active agent or said activated active agent.

5. The method of claim 3 wherein said second layer is a laminate of a non-ultrasonically sealable second member and an ultrasonically sealable third member, wherein said ultrasonically sealable third member of said second layer contacts said ultrasonically sealable first member, and said ultrasonically sealable third member and said non-ultrasonically sealable second member are permeable to said active agent or said activated active agent.

6. The method of claim 1 wherein said active agent is within said second layer.

7. The method of claim 1 wherein said active agent is within the space defined by said backing layer and second layer.

8. The method of claim 1 wherein said ultrasonic frequency is from about 19 kHz to about 21 kHz.

9. The method of claim 8 wherein said ultrasonic frequency is about 20 kHz.

10. The method of claim 1 wherein said ultrasonic frequency is applied for about 450 msec to about 750 msec.

11. The method of claim 1 wherein said pressure is about 389 lb to about 459 lb.

* * * * *